United States Patent
Mehta et al.

(10) Patent No.: US 9,349,220 B2
(45) Date of Patent: May 24, 2016

(54) CURVE CORRECTION IN VOLUME DATA SETS

(71) Applicants: KABUSHIKI KAISHA TOSHIBA, Tokyo (JP); Toshiba Medical Systems Corporation, Otawara (JP)

(72) Inventors: Nirav J. Mehta, Edinburgh (GB); Brady Anderson, Edinburgh (GB); Robert Lewis, Edinburgh (GB); John Zurowski, Edinburgh (GB)

(73) Assignees: KABUSHIKI KAISHA TOSHIBA, Tokyo (JP); TOSHIBA MEDICAL SYSTEMS CORPORATION, Otawara-shi (JP)

( * ) Notice: Subject to any disclaimer, the term of this patent is extended or adjusted under 35 U.S.C. 154(b) by 130 days.

(21) Appl. No.: 13/796,190

(22) Filed: Mar. 12, 2013

(65) Prior Publication Data

US 2014/0267220 A1 Sep. 18, 2014

(51) Int. Cl.
*G06T 15/00* (2011.01)
*G06T 19/20* (2011.01)
*G06T 15/08* (2011.01)
*G06F 19/00* (2011.01)

(52) U.S. Cl.
CPC .............. *G06T 19/20* (2013.01); *G06F 19/321* (2013.01); *G06F 19/3406* (2013.01); *G06T 15/08* (2013.01); *G06T 2210/41* (2013.01); *G06T 2215/06* (2013.01); *G06T 2219/028* (2013.01); *G06T 2219/2021* (2013.01)

(58) Field of Classification Search
CPC ..... G06T 19/20; G06T 15/08; G06T 2210/41; G06T 2219/028; G06T 2219/2021; G06T 2215/06; G06F 19/3406; G06F 19/321

USPC ............................ 345/419; 382/128; 600/410
See application file for complete search history.

(56) References Cited

U.S. PATENT DOCUMENTS 8,265,366 B2 * 9/2012 Dow et al. ...................... 382/128
8,315,689 B2 * 11/2012 Jenkins et al. ................. 600/410

* cited by examiner

*Primary Examiner* — Phu K Nguyen
(74) *Attorney, Agent, or Firm* — Oblon, McClelland, Maier & Neustadt, L.L.P.

(57) ABSTRACT

Certain embodiments provide a computer apparatus comprising a display and a processor running a visualization application for visualizing a three-dimensional patient image data set including an anatomical feature of interest. The visualization application is operable to: a) display on the display at least one view of the image data set together with a curve which is intended to follow a path relevant for the anatomical feature of interest, but which may include one or more deviations from the path; and b) initiate an editing session for the curve by selecting a portion of the curve associated with a deviation from the path for correction, the editing session comprising: (i) presenting an MPR view including the selected portion of the curve; (ii) defining a trend line which approximately follows the anatomical path in the vicinity of the selected portion of the curve; (iii) amending under user control any desired part of the selected portion of the curve in the MPR view to make corrections to the curve; (iv) rotating under user control the MPR view about a rotational axis which is parallel to the trend line in order to permit a user to review the corrections in three dimensions in the image data set; (v) iterating under user control the amending and rotating steps as desired to make and review further corrections; and (vi) terminating the editing session under user control by accepting or rejecting the corrections; and c) display at least one view of the image data set together with the curve incorporating amendments from the editing session.

21 Claims, 18 Drawing Sheets

| Saggital MPR | Curved MPR (CPR) | |
| --- | --- | --- |
| Coronal MPR | | |
| | P.H. | P.H. | P.H. |
| Transverse MPR | Cross-curve MPR | Volumetric |

Related Art

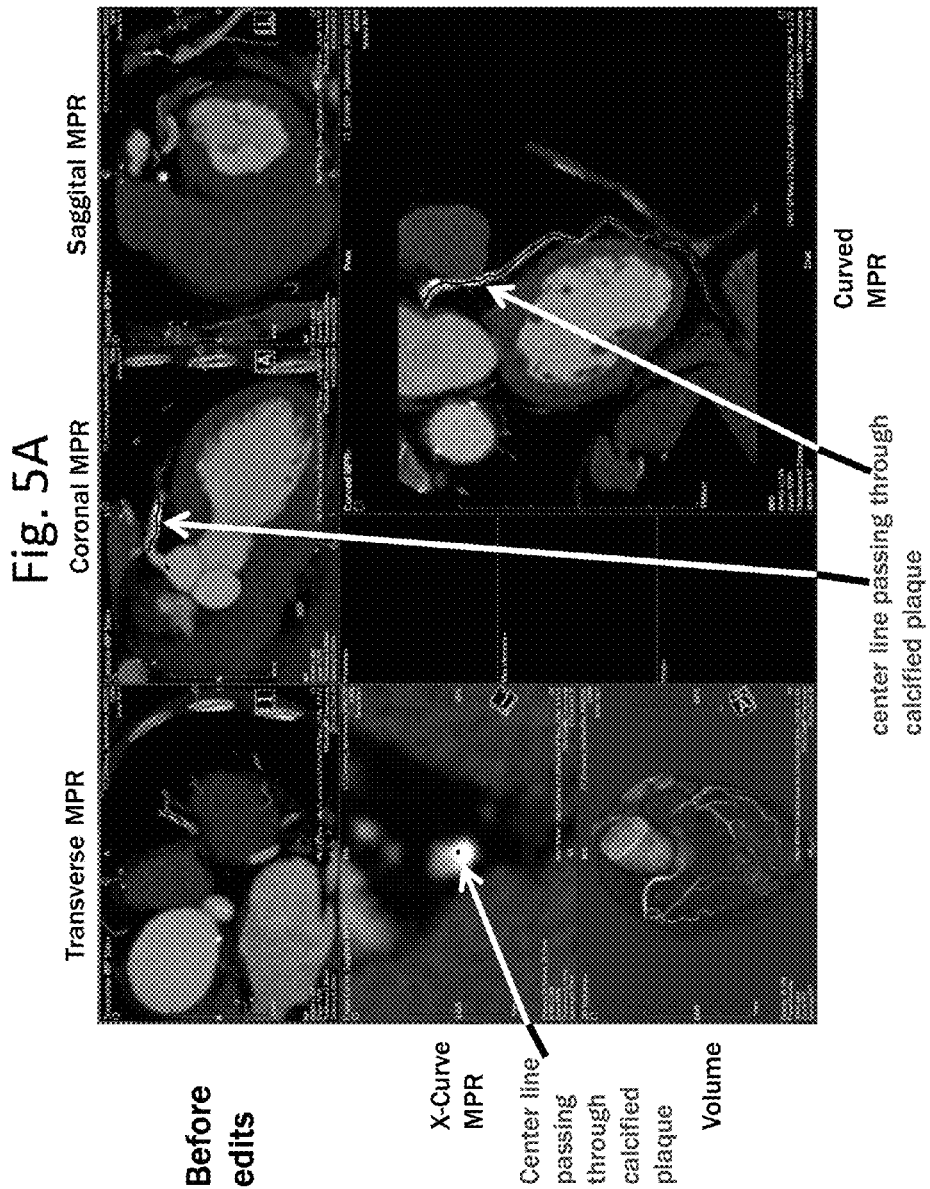

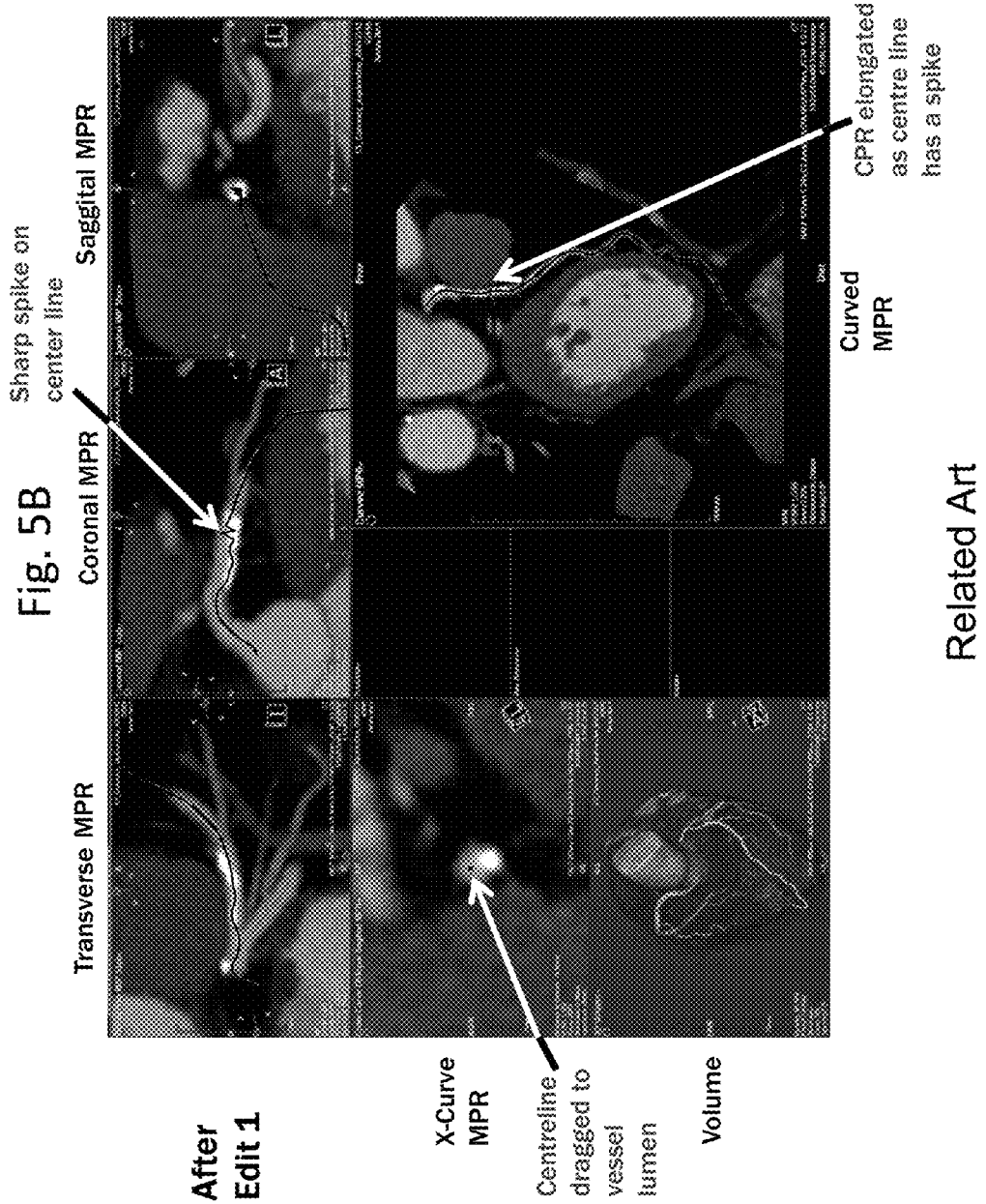

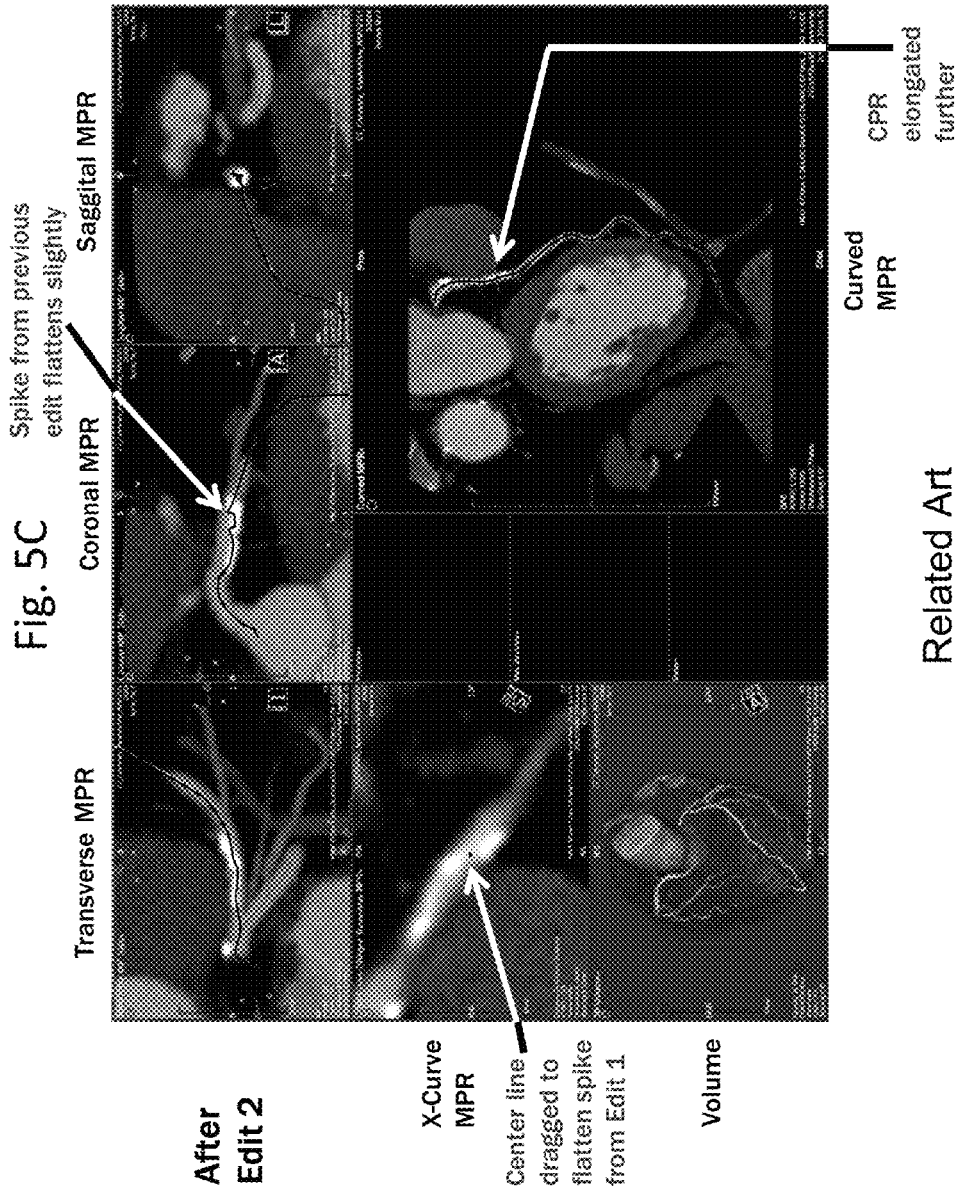

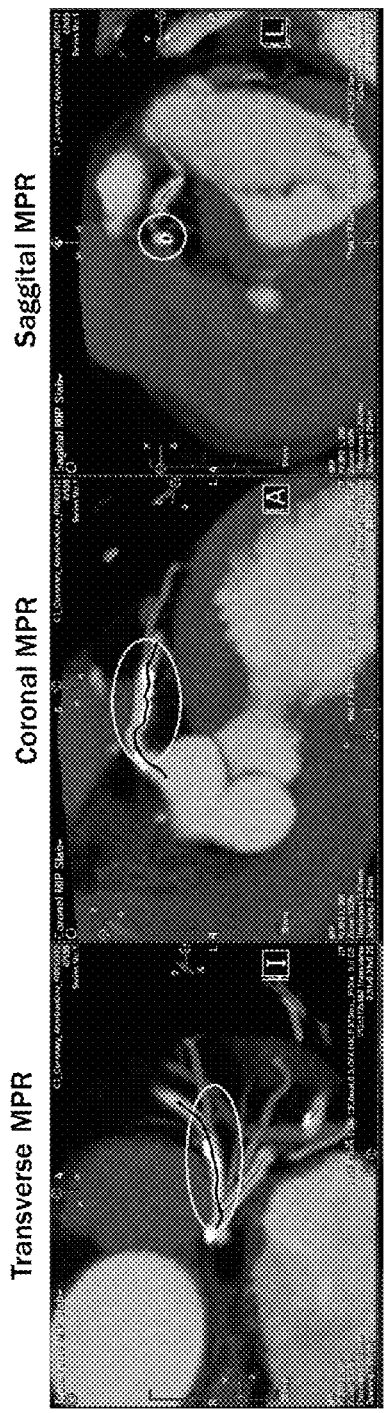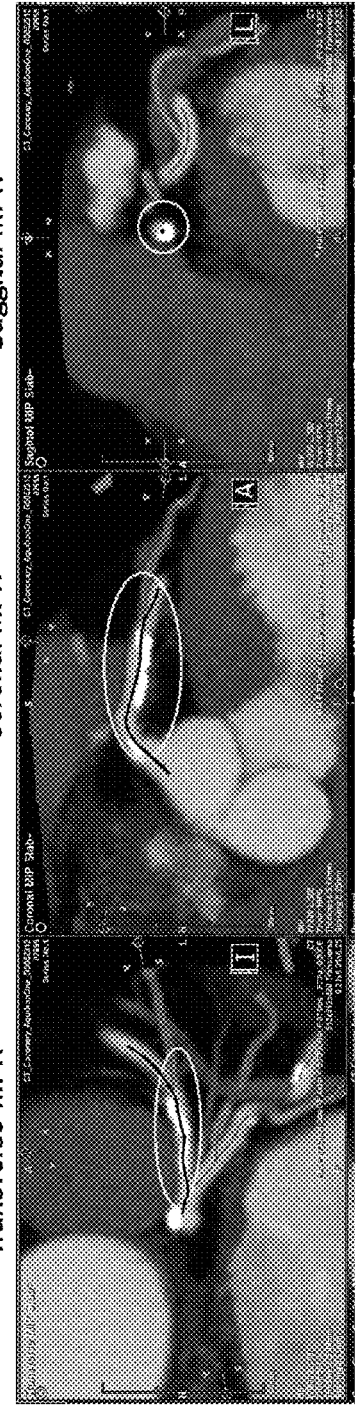
Fig. 6A Related Art
Fig. 6B Related Art

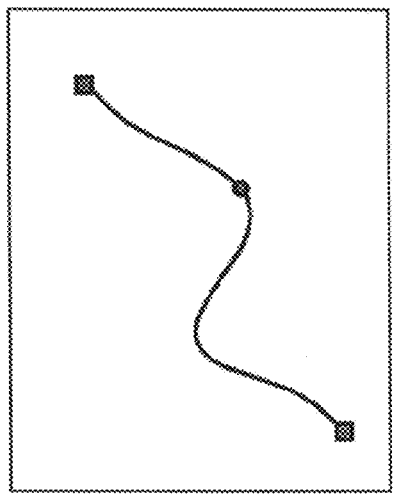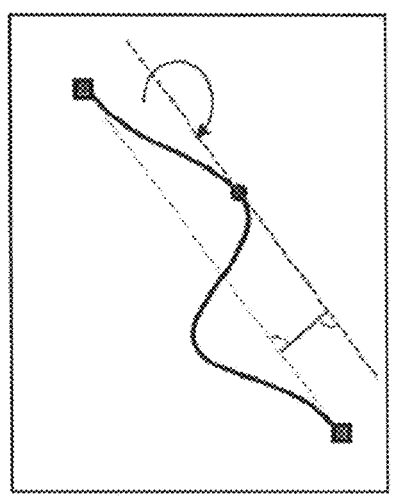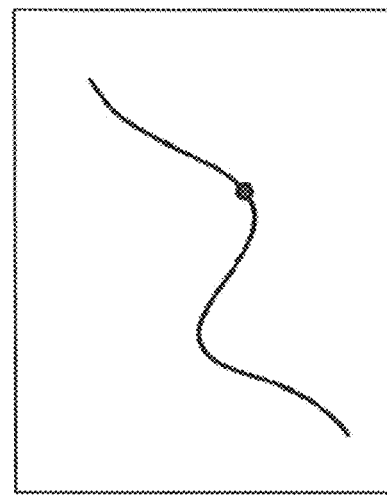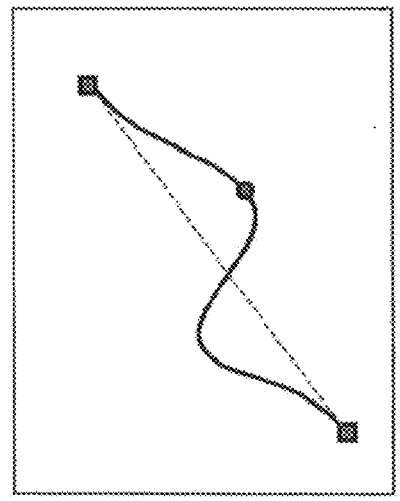

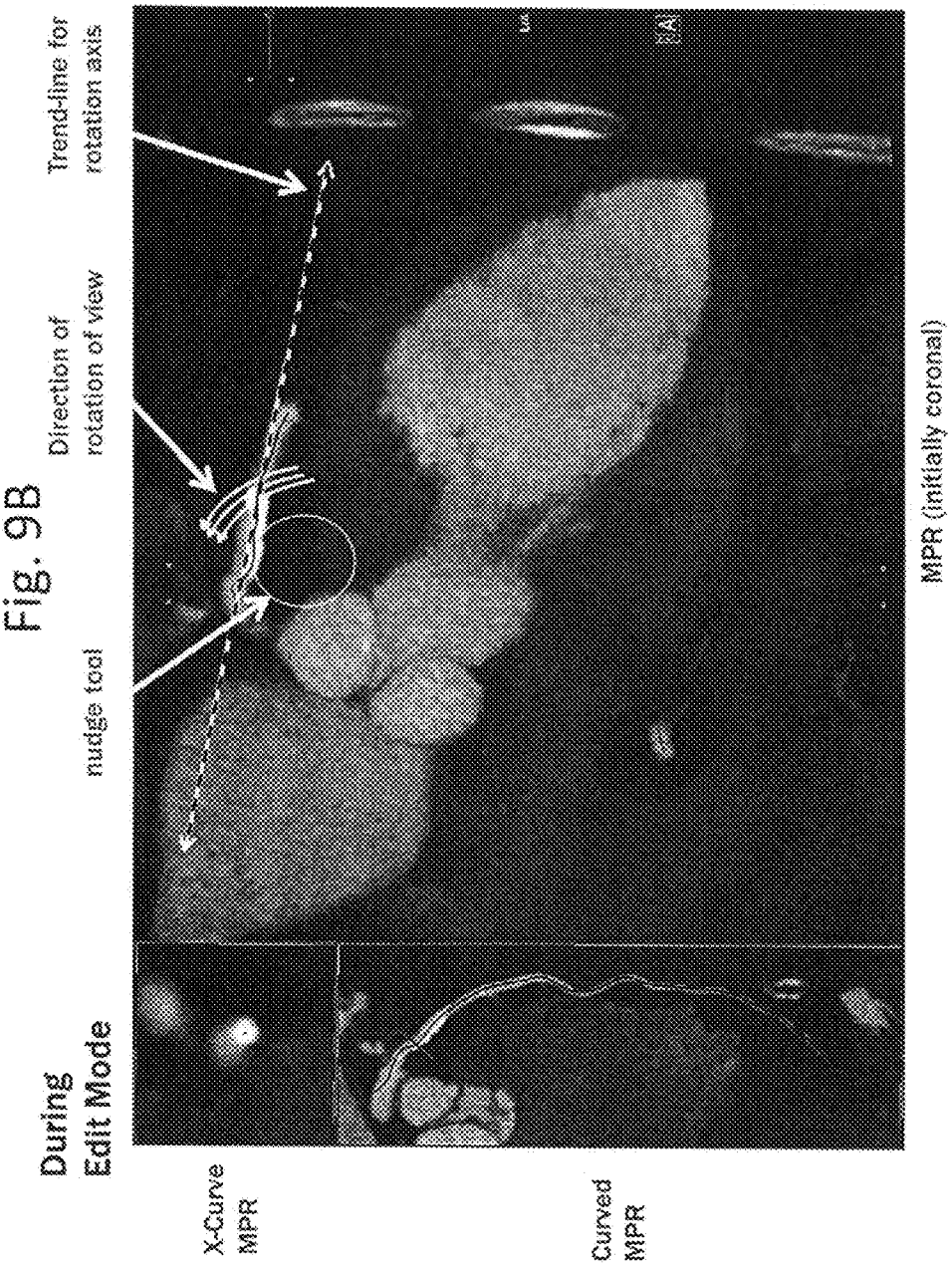

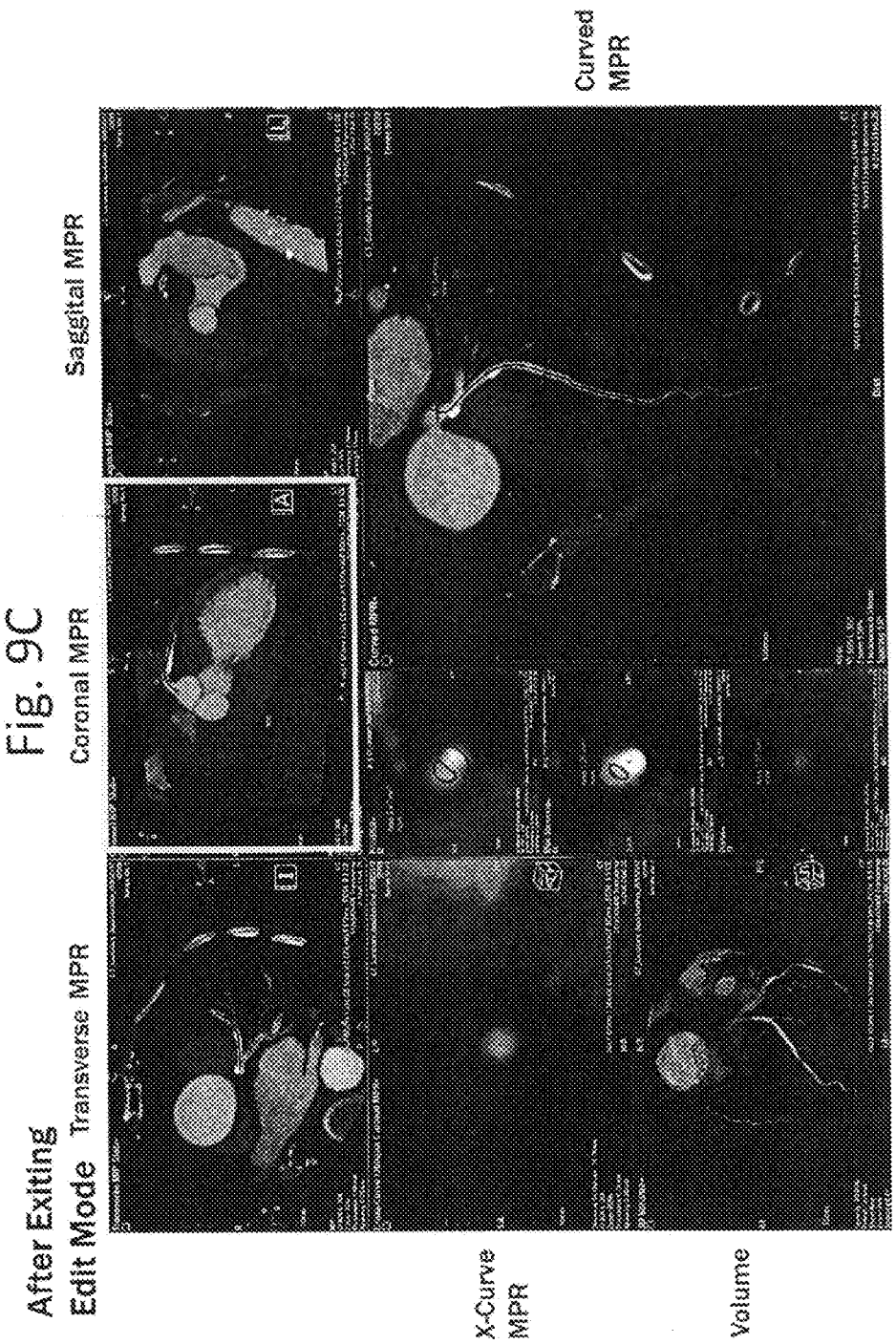

CURVE CORRECTION IN VOLUME DATA SETS

BACKGROUND OF THE INVENTION

Embodiments described herein generally relate to three-dimensional (3D) image data sets and in particular how to edit curves that follow a path relative to an anatomical feature of interest in 3D image data sets.

In the medical field, three-dimensional (3D) image data sets, i.e. volume data sets, are collected by a variety of techniques—referred to as modalities in the field—including computer assisted tomography (CT), magnetic resonance (MR), single photon emission computed tomography (SPECT), ultrasound and positron emission tomography (PET).

When displaying an image, particular signal values associated with an image data set can be associated with particular display brightness and also, in the case of non-grayscale images, colors to assist visualization. This association or mapping is performed when using data from a 3D data set (voxel data set) to compute a 2D data set (pixel data set) which represents a 2D projection of the 3D data set for display on a computer screen or other conventional 2D display apparatus. This process is known as volume rendering or more generally rendering.

A Widely Used Rendering Technique is Multi Planar Reformatting (MPR).

MPR is a way of presenting planar cross-sectional views through volume data to allow viewing of the data in any planar orientation independent of the orientation of the underlying data, which may have been collected in slices in the case of CT or MR.

However, in medical imaging many anatomical features of interest are non-planar. Consequently, a planar imaging method such as MPR is not always optimal, since a planar view may not allow visibility of a whole non-planar feature. For example, a surgeon may wish to study an artery along its entire length. The artery will follow a complex path in three-dimensions, so that any slice through the volume around the artery will only show part of it. The same problem arises for other curved anatomical structures, such as bronchi, the colon, the spine, and dental structures.

The technique of curved MPR was developed to address this limitation of conventional (planar) MPR.

Curved MPR allows curved planes to be defined within the data set and then viewed as a two-dimensional image. This allows, for example, curved, non-planar anatomical structures such as blood vessels or the colon, which cannot be fully seen in a single planar slice through the data set, to be shown in a single view. To generate the curved view, a three-dimensional curve which follows the structure of interest is defined through the volume data set representing the patient's body. The curved MPR view is then generated by extruding the curve in a particular direction to produce a curtain-like sheet in the three-dimensional volume, and then flattening the sheet and presenting it as a two-dimensional image.

It is noted that in the literature curved MPR is sometimes referred to as CPR (Curved Planar Reformatting).

Further views, known as cross-curve MPR views can be presented once the curve has been defined; these views are planar cross-sections through the data set which are perpendicular to the curve at a selected point.

By way of definition and to avoid confusion, any subsequent reference to "MPR" in this document which is not prefaced with "curved" or "cross-curve" is a reference to conventional, planar MPR.

Moreover, we use saggital, coronal and transverse according to their conventional medical definitions, for example when referring to particular views. Moreover, we use the term oblique to refer to a view or direction or plane which is not precisely saggital, coronal or transverse. Reference to an oblique MPR view is thus reference to an MPR view at an arbitrary viewing angle and in an arbitrary view plane. Reference to an oblique transverse view means a view that is substantially, but not exactly, transverse.

In the case of a vessel, intestine or other generally tubular anatomical feature, the curve relevant for the curved MPR view is a centerline. For other structures, such as to follow the curvature of the spine or to follow the line of teeth around a jaw, the term centerline is perhaps a less appropriate label for the curve.

By way of definition we use the term lumen as a generic label for a tubular organ, such as a blood vessel, artery or vein, or an intestine or the colon. To find the centerline of a lumen it is standard practice to use an automatic centerline finding algorithm. Since a curved MPR view is based on the centerline, any errors in the centerline relative to the underlying anatomical feature of interest are likely to cause the curved MPR image to appear differently to how the viewer imagines it should.

FIG. 1 illustrates one common type of error produced by an automated centerline finding algorithm for an artery. Bends in the artery cause the automatic centerline finding algorithm used here to cut the corner. The centerline algorithm is said to have followed a "racing line" around the bend—which means moving away from the center of the artery and approaching the apex of the bend. With a racing line around a bend, and assuming the artery has a perfectly circular diameter which is constant along its length, the curved MPR view will show that the artery diameter reduces (or enlarges) where there are bends, but the position of the bends and how tight they are will not necessarily be clear from the curved MPR view. Consequently in the curved MPR view, the diameter variations in the artery may not appear to be simply correlated with bends. To the clinician, the artery therefore may appear to have a stenosis (or aneurysm) when it is in fact perfectly healthy.

FIGS. 2 and 3 illustrate another common type of error produced by an automated centerline finding algorithm for an artery when areas of the artery wall have significant plaque deposits. Each of FIG. 2 and FIG. 3 is a collection of views (transverse MPR, coronal MPR, cross-curve MPR and curved MPR view) of an artery with the centerline computed by an automatic centerline finding algorithm marked and shown as a dark line, and a portion of the artery with a plaque-induced error circled.

Some automatic centerline finding algorithms will tend to confuse the plaque with the artery's tubular structure, and thus the centerline will jump from the center of the artery where there is no plaque, to the center of the plaque where there is significant plaque on one side of the artery. Moreover, since the plaque may be at any angular position on the artery wall as viewed in cross-section, the centerline can randomly move around the wall in a kind of zig-zag spiral. The plaque-induced centerline error is shown in an extreme form in the cross-curve MPR views of FIGS. 2 and 3, where the plaque is white and the artery is gray. It is evident that the centerline is in the middle of the plaque and on the very edge of the artery. In the coronal MPR views of FIGS. 2 and 3, the zig-zag effect of following the plaque is visible and it is quite clear that the centerline is misplaced. On the other hand, in the transverse MPR views of FIGS. 2 and 3, the centerline gives the false impression of being roughly correct.

The complex and non-intuitive nature of the transform involved with curved MPR and its relation to any errors in the centerline make this a really difficult problem from the user perspective. For example, a bend might be visible in the curved MPR view which is somewhat similar to the real bend, but not the same. This is because a curved MPR view does not simply straighten out a curve, the curved MPR computation being more complex than that. A user tends to think of a curved MPR view as a (planar) MPR view which has a viewing direction parallel to the viewing direction from which the standard MPR plane (coronal, saggital or transverse) is displayed, since this helps the user to put the curved MPR image into context within the patient. However, this way of thinking is a false friend when it comes to the user comparing the curved MPR view with the actual underlying data. In the general case, it is simply beyond a normal user's intuition to follow the transform that has been carried out to compute the curved MPR view and at the same time think about how different kinds of common errors in the centerline positioning will distort the curved MPR view.

Because of these known problems, it is necessary for the centerline computed by the automated centerline finding algorithm to be reviewed by an expert and if necessary manually corrected by intervention via the graphical user interface (GUI). The GUI is provided with standard CAD (computer aided design) tools to aid the editing. An editing session will include identification of a portion of the centerline that needs to be corrected and provision of a graphical user interface tool, such as a "nudge" tool, to allow the centerline to be moved.

Reviewing and editing centerlines computed by an automatic centerline finding algorithm is quite time consuming with the editing tools provided in existing rendering applications. Moreover, the existing editing tools can be confusing. Because of these factors, the review and editing of centerlines computed by automatic centerline finding algorithms is typically delegated by the clinician to a technician.

Some existing editing solutions are based on editing the centerline in the cross-curve MPR or curved MPR views. For example, the rendering application "syngo" (registered trade mark) marketed by Siemens Medical Systems, Inc. offered such a feature in version "CT 2005A".

FIG. 4 shows the layout of views used in several subsequent figures, which is one potential layout for a rendering/visualisation application. Transverse, coronal and saggital MPR views are shown in a strip from left to right at the top of the display. A curved MPR view is shown larger than the other views on the right lower part of the display. On the left middle part of the display, a cross-curve MPR view is shown, and on the left lower part of the display a volumetric view is shown which is a perspective view with significant saggital, coronal and axial components. The smallest views are three views labeled P.H. and these are placeholders for stenosis measurement views associated with this particular example layout.

An example editing session based on editing the cross-curve MPR view is now described.

FIGS. 5A, 5B and 5C are screen shots in the format of FIG. 4. FIGS. 5A, 5B and 5C illustrate an example centerline editing session based on editing the cross-curve MPR views. FIG. 5A shows the starting state before the editing session is commenced, FIG. 5B shows the layout after a first edit. FIG. 5C shows the layout after a second edit.

In FIG. 5A, the centerline has passed through some calcified plaque and needs to be moved to its correct position following the artery's true centerline. To make the correction, the user initiates an editing session and, as shown in FIG. 5B, drags the centerline to the center of the vessel lumen with the aid of the cross-curve MPR view. However, as can be seen in the coronal MPR view of FIG. 5B, this manipulation has caused a sharp spike in the centerline, i.e. a new error. Moreover, this spike has caused artificial elongation of the curved MPR view. To correct the spike, as shown in FIG. 5C, the user changes the cross-curve MPR view from oblique saggital to oblique transverse and flattens out the spike by dragging the centerline in this view. The drag has the desired effect on the spike, but further artificially elongates the curved MPR view.

The basic problem which this example shows is that, since cross-curve MPR views (and also curved MPR views) are themselves by-products of the existing centerline, editing these views is inherently likely to cause confusion to the user. It is not uncommon that an attempt to correct a portion of the centerline reaches such a confused state that the user has to restart the editing session.

FIGS. 6A and 6B are screen shots of the top row of views in the layout of FIG. 4 which illustrate an example centerline editing session based on editing the coronal MPR view. FIG. 6A shows the standard planar MPR views (transverse, coronal, sagittal) before an edit. FIG. 6B shows the same views after the edit.

In FIG. 6A, the user sees that the centerline seems roughly (although nor perfectly) correct in the transverse MPR view, but shows significant plaque error in the coronal MPR and sagittal MPR views, where plaque appears bright white and the artery gray. For example, in the coronal view the computed centerline can be seen as being below the true centerline of the artery. In the transverse view the computed centerline can be seen as being more jagged than the true centerline of the artery. The user therefore edits the centerline in the coronal MPR view to follow the artery, not the plaque, as shown in the coronal MPR view of FIG. 6B. The coronal MPR view of FIG. 6B shows some improvement in the centerline position compared with FIG. 6A, but still does not look accurate. However, the transverse MPR view of FIG. 6B, clearly shows the edit has not corrected the centerline completely, since in the transverse MPR view the centerline is still zig-zagging (for example as compared to the transverse and saggital views) to follow plaque. In this example, some positive progress appears to have been made, but clearly the user has more work to do, for example by editing the transverse MPR view.

For editing the centerline using these known approaches, the user therefore needs clear visibility of effects of the centerline edits he is making in the corresponding planes. Due to lack of screen space the user may need to modify the display to in effect magnify the region of interest. For example, the user might need to expand the window containing the view of interest by in effect taking screen space from other views, and potentially "covering" the other views entirely with the expanded view of interest. Alternatively, or in addition, the user might zoom in on a smaller part of the view of interest. However, both these approaches can be inconvenient and cumbersome. For example, with the first approach the user will need to cycle through the different views in series to try to assess the overall impact of the edits in multiple planes (because he can no longer see all views at once). With the second approach, the user may be unable to see the entire portion of centerline of interest at one time and so need to make amendments iteratively for different portions of the centerline in the same view plane.

BRIEF DESCRIPTION OF THE DRAWINGS

Embodiments of the invention are now described by way of example only with reference to the following drawings.

FIG. 4 shows a layout of views used in several subsequent figures, which is one potential layout for a rendering application.

FIGS. 5A, 5B and 5C are screen shots in the layout of FIG. 4 which illustrate an example centerline editing session based on manipulation of the cross-curve MPR view.

FIGS. 6A and 6B are screen shots of the top row of views in the layout of FIG. 4 which illustrate an example centerline editing session based on editing the coronal MPR view.

FIGS. 8A, 8B, 8C and 8D schematically represent the establishment of a trend line in step S5 of the flow diagram represented in FIG. 7 in accordance with some embodiments of the invention.

FIGS. 9A, 9B and 9C are example screen shots before, during and after an example editing session according to FIG. 7.

DETAILED DESCRIPTION

Figure 1:
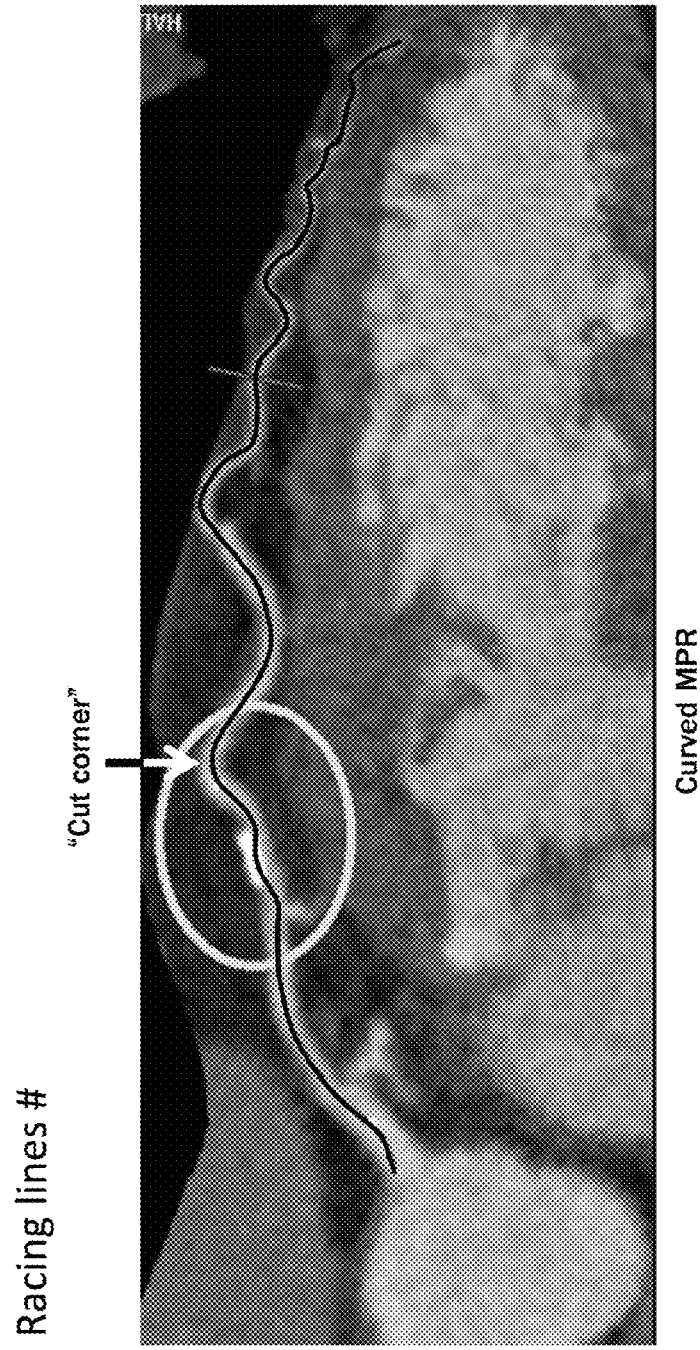
FIG. 1 is a curved MPR view of an artery with the centerline computed by an automatic centerline finding algorithm marked and shown in dark line, and a portion of the artery with a racing line error circled.
Figure 2:
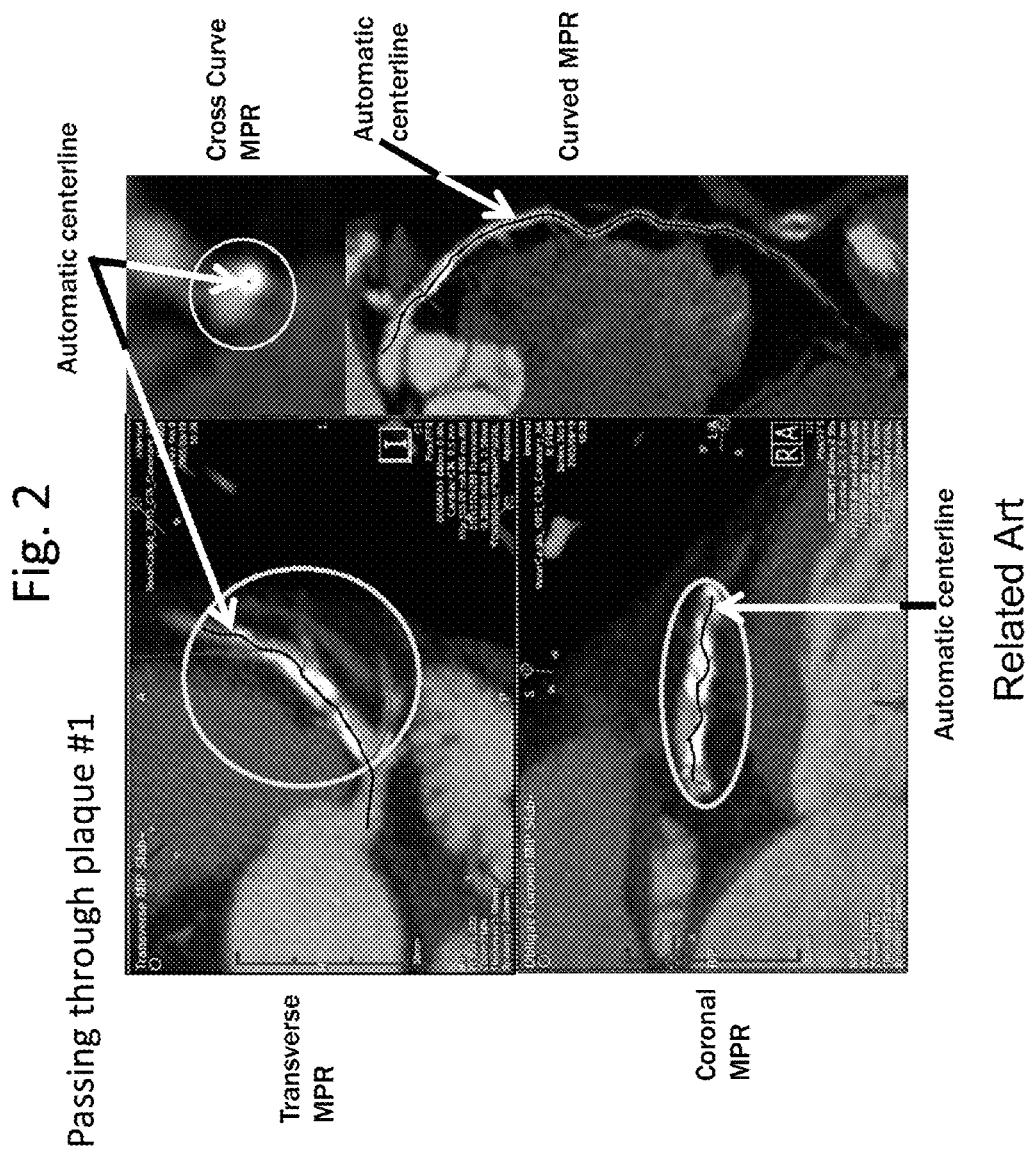
FIG. 2 is a collection of views (transverse MPR, coronal MPR, cross-curve MPR and curved MPR view) of an artery with the centerline computed by an automatic centerline finding algorithm marked and shown in dark line, and a portion of the artery with a plaque-induced error circled.
Figure 3:
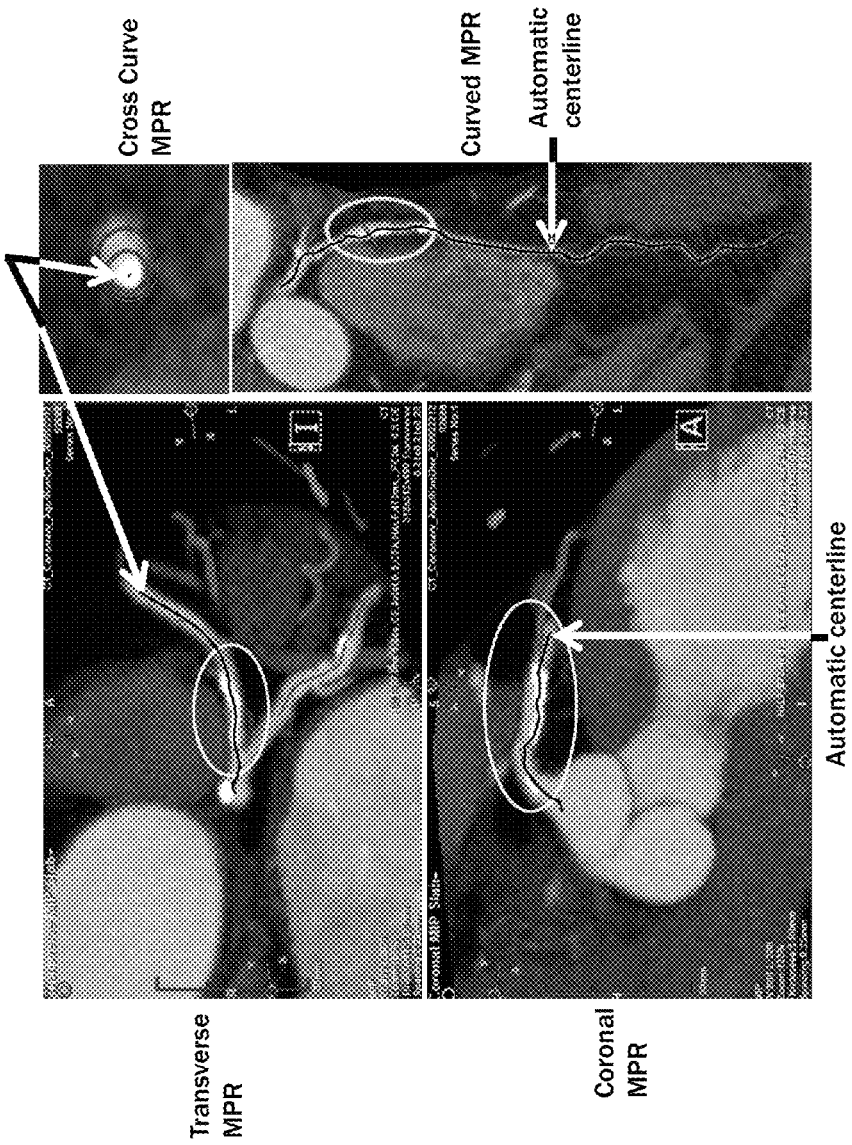
FIG. 3 is similar to FIG. 2 providing another example of plaque-induced error in the centerline.

Certain embodiments provide a computer apparatus comprising a display and a processor running a visualization application for visualizing a three-dimensional patient image data set including an anatomical feature of interest. The visualization application is operable to: a) display on the display at least one view of the image data set together with a curve which is intended to follow a path relevant for the anatomical feature of interest, but which may include one or more deviations from the path; and b) initiate an editing session for the curve by selecting a portion of the curve associated with a deviation from the path for correction, the editing session comprising: (i) presenting an MPR view (which might in accordance with certain embodiments be a thin MPR view or a slab MPR view) including the selected portion of the curve; (ii) defining a trend line which approximately follows the anatomical path in the vicinity of the selected portion of the curve; (iii) amending under user control any desired part of the selected portion of the curve in the MPR view to make corrections to the curve; (iv) rotating under user control the MPR view about a rotational axis which is parallel to the trend line in order to permit a user to review the corrections in three dimensions in the image data set; (v) iterating under user control the amending and rotating steps as desired to make and review further corrections; and (vi) terminating the editing session under user control by accepting or rejecting the corrections; and c) display at least one view of the image data set together with the curve incorporating amendments from the editing session.

In accordance with certain embodiments the visualization application is operable such that as part of initiating an editing session the user selects a particular view from the at least one view of the image data to be presented initially which shows the selected portion of the curve that requires correction.

In accordance with certain embodiments the anatomical feature of interest is a tubular structure and the anatomical path is a centerline of the tubular structure which the curve is intended to follow.

In accordance with certain embodiments the rotational axis is offset from the trend line to pass through the vicinity of amended parts of the selected portion of the curve.

In accordance with certain embodiments the visualization application is operable such that during an editing session the rotational axis is free to move to remain in intersection with, or close to intersection with, amended parts of the selected portion of the curve.

In accordance with certain embodiments the visualization application is operable such that the trend line is automatically computed from points on the curve at either end of the selected portion of the curve.

In accordance with certain embodiments the visualization application is operable such that during the editing session the MPR view is presented on the display along with a curved MPR view and/or a cross-curve MPR view updated to follow said rotation.

In accordance with certain embodiments the visualization application is further operable to store in memory associated with the computer apparatus the three-dimensional patient image data set with an indication of the curve in its edited form, or to output the three-dimensional patient image data set with an indication of the curve in its edited form for external storage.

In accordance with certain embodiments the visualization application is operable such that the amending is carried out with a graphical user interface control using a circle of adjustable diameter as a geometric construct, the circle being translatable in the plane of the MPR view to come into contact with the curve, whereupon the curve is amended to conform to the contacting edge portion of the circle.

Certain embodiments provide a computer-automated method of running a visualization application on a computer apparatus to visualize a three-dimensional patient image data set including an anatomical feature of interest, the method comprising: a) displaying at least one view of the image data set together with a curve which is intended to follow a path relevant for the anatomical feature of interest, but which may include one or more deviations from the path; b) initiating an editing session by selecting a portion of the curve associated with a deviation from the path for correction, the editing session comprising: (i) presenting an MPR view including the selected portion of the curve; (ii) defining a trend line which approximately follows the anatomical path in the vicinity of the selected portion of the curve; (iii) amending under user control any desired part of the selected portion of the curve in the MPR view to make corrections to the curve; (iv) rotating under user control the MPR view about a rotational axis which is parallel to the trend line in order to permit a user to review the corrections in three dimensions; (v) iterating under user control the amending and rotating steps as desired to make and review further corrections; and (vi) terminating the editing session under user control by accepting or rejecting the corrections; and then c) displaying at least one view of the image data set together with the curve incorporating amendments from the editing session.

Certain embodiments provide a computer program product storing a visualization application operable to: a) display on a display of a computer at least one view of an image data set together with a curve which is intended to follow a path relevant for an anatomical feature of interest represented in the data set, but which may include one or more deviations from the path; and b) initiate an editing session for the curve by selecting a portion of the curve associated with a deviation from the path for correction, the editing session comprising: (i) presenting an MPR view including the selected portion of the curve; (ii) defining a trend line which approximately follows the anatomical path in the vicinity of the selected portion of the curve; (iii) amending under user control any desired part of the selected portion of the curve in the MPR view to make corrections to the curve; (iv) rotating under user control the MPR view about a rotational axis which is parallel to the trend line in order to permit a user to review the corrections in three dimensions in the image data set; (v) iterating under user control the amending and rotating steps as desired to make and review further corrections; and (vi) terminating the editing session under user control by accepting or rejecting the corrections; and c) display at least one view of the image data set together with the curve incorporating amendments from the editing session.

Certain embodiments provide an image acquisition device loaded with and operable to execute a visualization application operable to: a) display on a display of a computer at least one view of an image data set together with a curve which is intended to follow a path relevant for an anatomical feature of interest represented in the data set, but which may include one or more deviations from the path; and b) initiate an editing session for the curve by selecting a portion of the curve associated with a deviation from the path for correction, the editing session comprising: (i) presenting an MPR view including the selected portion of the curve; (ii) defining a trend line which approximately follows the anatomical path in the vicinity of the selected portion of the curve; (iii) amending under user control any desired part of the selected portion of the curve in the MPR view to make corrections to the curve; (iv) rotating under user control the MPR view about a rotational axis which is parallel to the trend line in order to permit a user to review the corrections in three dimensions in the image data set; (v) iterating under user control the amending and rotating steps as desired to make and review further corrections; and (vi) terminating the editing session under user control by accepting or rejecting the corrections; and c) display at least one view of the image data set together with the curve incorporating amendments from the editing session.

Figure 7:
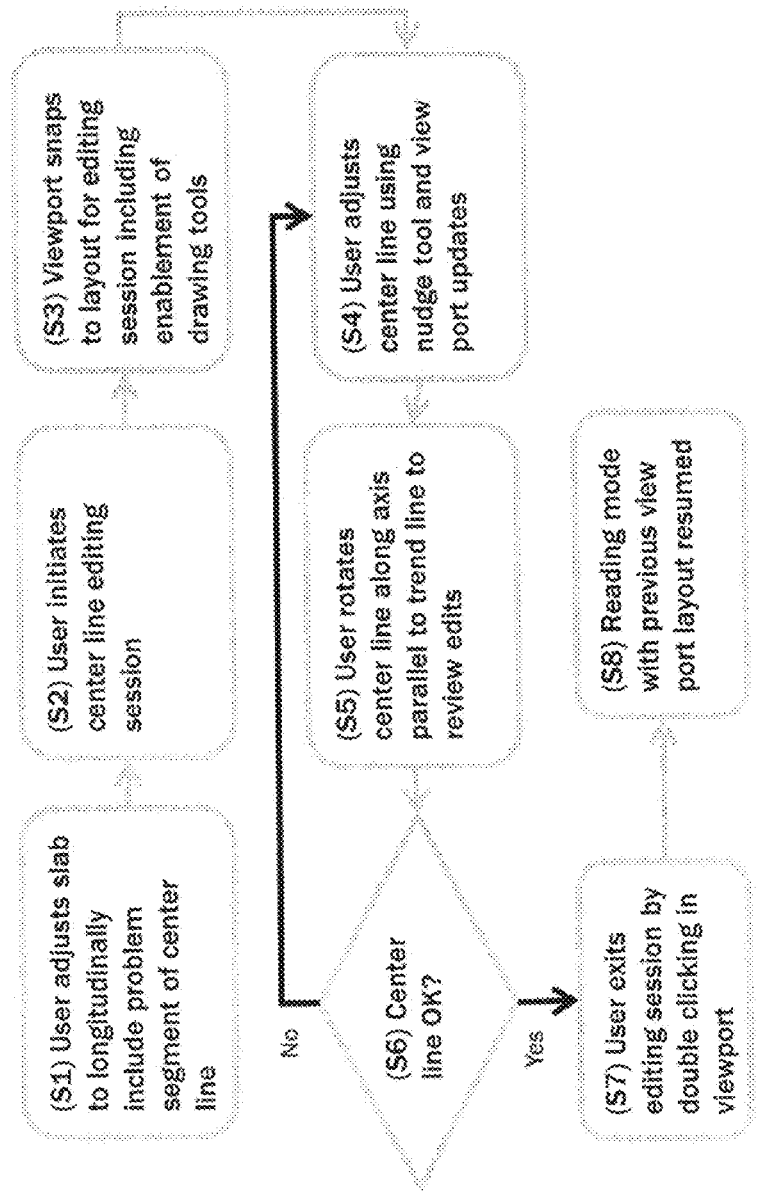
FIG. 7 is a flow diagram showing steps of a curve editing session according to an embodiment of the invention.

FIG. 7 is a flow diagram showing steps of a method of curve editing according to an embodiment of the invention.

The method is initiated when the user, during view of a multi-view display layout, such as the layout of FIG. 4, identifies a portion or segment of centerline that is inaccurate, in that the centerline does not accurately follow the path it is supposed to down the middle of the lumen, but includes one or more deviations from the true path, i.e. the ground truth path.

In Step S1, the user adjusts the transverse, coronal, sagittal or oblique MPR views, which might include adjustments to MPR slab thickness, so that the segment of centerline in need of correction is evident in a single MPR view (transverse, coronal, saggital or oblique). This ensures that at the start of an editing session, an MPR view is displayed which shows all of the selected portion of the centerline that requires correction. (It will be appreciated these various MPR views may be single or slab MPR views.)

In Step S2, the user actuates a control to initiate a centerline editing session. The control may be a keyboard shortcut or a button on the display for example. The actuation will include selection of a desired view in which, not only the whole centerline portion to be corrected is visible, but also the view in which the nature of the error is clear. With a cursor control, the user clicks on a point on the centerline curve to be corrected (see curve of FIG. 8A), which defines what might be referred to as a mid-point for the error under consideration on the centerline (see circular symbol in FIG. 8A). A length portion of the centerline is then defined with reference to the identified error mid-point. For example, the portion may be defined by two end points lying on the centerline on either side of error mid-point and separated from it by a predefined distance (as measured along the centerline itself or as the crow flies). Example end (bounding) points are represented by square symbol points in FIG. 8B). In other example embodiments the length portion of the centerline to be corrected could be identified manually by a user clicking on these two bounding points directly, potentially without the user first defining an error mid-point which could then be computed from the bounding points. A notional straight line intersecting the two bounding points, which can be referred to as a trend line for the portion to be edited, is then computed (see dashed line in FIG. 8C). The purpose of computing the trend line is to establish a general direction of extent for the lumen (or other anatomical feature of interest) in the vicinity of the centerline portion to be edited. As such, other methods of defining the trend line could be used. Furthermore, if the MPR is slabbed, as is common, then the boundary points can be limited to the extent of the visible curve portion inside the slab containing the centerline portion to be edited, e.g. to represent the slab boundaries, or if a particular boundary point would be outside the slab to clip its value to the slab boundary.

In Step S3, upon user selection of the centerline edit control, the display changes to a layout showing the selected MPR view with the trend line in a magnified manner. Although not essential, some implementations may include a curved MPR view and/or a cross-curve MPR view in addition to the planar MPR view, and may update these views as well as the (planar) MPR view continually during the editing session to give visual feedback to the user. A circle is also shown which is the visible manifestation of a nudge object which is part of a nudge tool. The circle is a 2D nudge object having a user-defined diameter. By moving the circle so that an edge portion touches a part of the centerline, that part of the centerline intersecting the arc is nudged, i.e. moved, to conform to the arc. A small diameter nudge circle will cause more localized correction of the curve than a larger diameter nudge circle. The diameter of the circle can be automatically set to an initial value equal to the distance from where a user clicks to place the center of the circle and the smallest distance to the centerline. One example of how to control the nudge is that, if a particular mouse button is held down and the circle meets the centerline, the centerline is adjusted to match the intersecting arc of the circle, whereas, if that mouse button is up (i.e. not being held down) and the circle meets the line, then the diameter of the circle decreases as the cursor moves further towards the line (or increases as the cursor moves away from the line). The diameter of the circle may also be capped to a maximum value. Nudge tools are known CAD tools and are not described further. For example, one known nudge tool is the so-called 'repulsor tool' included in recent MAC OS versions of OsiriX—a well-known open source rendering application for DICOM files.

In Step S4, the user adjusts a portion of the centerline using the nudge tool or other suitable curve editing tool. Other example curve editing tools might be a drag tool. A drag tool is a tool that can be used to pull centerlines in a localized region, wherein the length of the affected portion of the centerline can be varied according to the extent and direction of the drag. An example implementation of a drag tool would be, if the cursor is on or near a point on the centerline and a particular mouse button is held down, then the point on the centerline and adjacent points up to a maximum extent are free to move in a smooth and appropriate way in response to subsequent movement of the cursor.

Another example curve editing tool would be a tool that interpolates between the bounding points either very simply, e.g. with a straight line between the bounding points or other points closer to the error mid-point, or by taking account of portions of the centerline outside the selected portion to be edited with a higher order polynomial interpolation. The MPR view and optional curve and cross-curve MPR views are updated in real time.

In Step S5, the centerline is in effect rotated about a rotational axis defined as a line parallel to the trend line and intersecting the error mid-point (see FIG. 8D) to review the effect of the curve editing through preferably an entire 360 degree rotation, but at least different rotational angles spread over a wide angular range. The MPR view showing the centerline updates during the rotation, i.e. for each selected angle around the rotational axis. That is to say, the view direction for the rendering of the MPR view showing the centerline is moved around the rotation axis so the user in effect views the center line from different directions as the centerline is rotated about the rotational axis. Consequently the rotations about the rotational axis may show MPR views at different arbitrary rotational angles (i.e. not in the same plane as originally selected MPR view). If also included in the editing session layout, the curved MPR view and/or cross-curve MPR view are in this example also updated during the rotation. The inventors have recognized that this approach can help readily provide feedback to a user on how edits/corrections made to a centerline as represented in one MPR view have an impact on the representation of the centerline in other planes of a 3D volume.

In other examples the rotational axis could be taken to be the axis parallel to the trend line and intersecting the point (or centroid of a group of points) on the centerline that have been edited (e.g. moved by the nudge tool) in the editing session, or edited recently in the editing session. In still another alternative the rotational axis could be taken to be fixed as the axis parallel to and coincident with the trend line.

Regardless of the specific rotation axis selected in a given implementation, the effect to be achieved in accordance with certain embodiments of the invention is rotation about an axis that runs through the vicinity of the part of the centerline that is being edited and an axis that generally is directed in the direction of the underlying anatomical feature. The user can stop at any particular rotational angle and use the nudge tool again to make further adjustments to the centerline as desired. It is preferred that the rotation appears to be continuous, i.e. is quasi-continuous in sufficiently small angular increments, for example increments of 1, 2, 3, 4, 5, 6, 7, 8, 9, 10, 15, 20, 30 or 45 degrees. The rotational speed may be fixed or adjustable by a user control. The user interface controls may also allow the user to revert to the initial MPR view at the beginning of the session (which will typically be coronal, saggital or transverse) and jump to an orthogonal MPR view from the initial MPR view (which will be another of coronal, saggital or transverse in the case that the initial view is one of these standard views).

In Step S6 the user is prompted to answer the question of whether the centerline is now satisfactory, i.e. looks to be accurate in the 'custom' MPR view for a full range of rotation, as well as in the curve and cross-curve MPR views for a full range of rotation if these are included. If 'no', then the flow returns to Step S4 to permit further curve editing. If 'yes', the correction is deemed to be satisfactory and the flow continues to Step S7. It will be appreciated that in other examples there might be no explicit prompt asking the user to confirm this. Rather, the user may simply exit the editing session (e.g. as discussed further below in relation to Step S7) when the user considers the centerline to be satisfactory. In this case, the visualisation application may simply be configured to allow a user to make edits/adjustments to the centerline and to view rotations of the centerline continuously until the editing session is exited.

In Step S7, the user indicates completion of the editing session of this particular centerline portion, and the editing session is terminated. This can be achieved for example by simply double clicking in the view port. Different controls are provided for the options of accepting or rejecting the edits.

In Step S8, after the centerline editing mode is exited, the user is returned to the previous layout to resume review of the data.

It is noted for certain embodiments in accordance with the implementation represented in FIG. 7, for a particular editing session the rotational axis is free to move parallel to the trend line depending on whereabouts along the centerline is deemed to be most relevant—typically the point or length portion along the centerline where the corrections are currently being made. During a particular editing session, the rotational axis thus moves so that it remains in intersection with, or close to intersection with, amended parts of the selected portion of the centerline.

In the example discussed above, the trend line is automatically computed from points on the curve at either end of the selected portion of the curve. In other examples, different automatic computation methods may be used for defining the trend line. In still further examples, the position and direction of the trend line may be fixed by user manipulation of graphical user interface controls, or at least the user may be provided with a user interface control which allows adjustment of an automatically computed trend line.

In the current implementation, during a given editing session, the trend line may be re-computed whenever a new editing location is established (for example in accordance with the process described above with reference to FIGS. 8A to 8C). However, in other implementations, the trend line might remain fixed for all or part an editing session once the trend line has been established (for example in cases where endpoints of the kind represented in FIG. 8B are not re-established in response to a change in editing point).

It is further noted that in slab MPR, the slab thickness will generally be set to be approximately the same as the thickness of the anatomical feature of interest, so in the case of vessels perhaps a little larger than the vessel diameter, which for cardiac vessels may be a few millimeters.

A refinement of the method would be to incorporate so-called auto-slabbing of the MPR to ensure the portion of the centerline of interest remains visible. For example, the slab thickness could be automatically changed during rotation in Step S5 to ensure the centerline portion of interest, i.e. between the boundary points, remains visible at all rotational angles. Auto-slabbing could also be used earlier in the process at Step S2 to define the slab thickness based on where the user defines the boundary points.

In summary, the above method provides a simple, quick and reliable method of correcting a centerline based on a single layout with a limited number of views, in an extreme case displaying to the user only one MPR view, and in other cases additionally displaying a curved MPR view and/or a cross-curve MPR view.

The method avoids problems associated with editing centerlines in curved MPR views which is a fundamentally flawed approach given that a user in general can have no simple appreciation of the underlying data owing to the non-intuitive sophisticated nature of the transforms used to generate curved MPR views. Compared with limitations associated with editing centerlines in a single fixed MPR view, the concept of rotation of the MPR view about an axis in the general direction of the lumen provides enough freedom to make the correction in a single, readily understandable MPR view while being able to see the effects of the correction in three dimensions during editing in a single view.

An example editing session is now described with reference to FIGS. 9A, 9B and 9C.

Figure 9A:
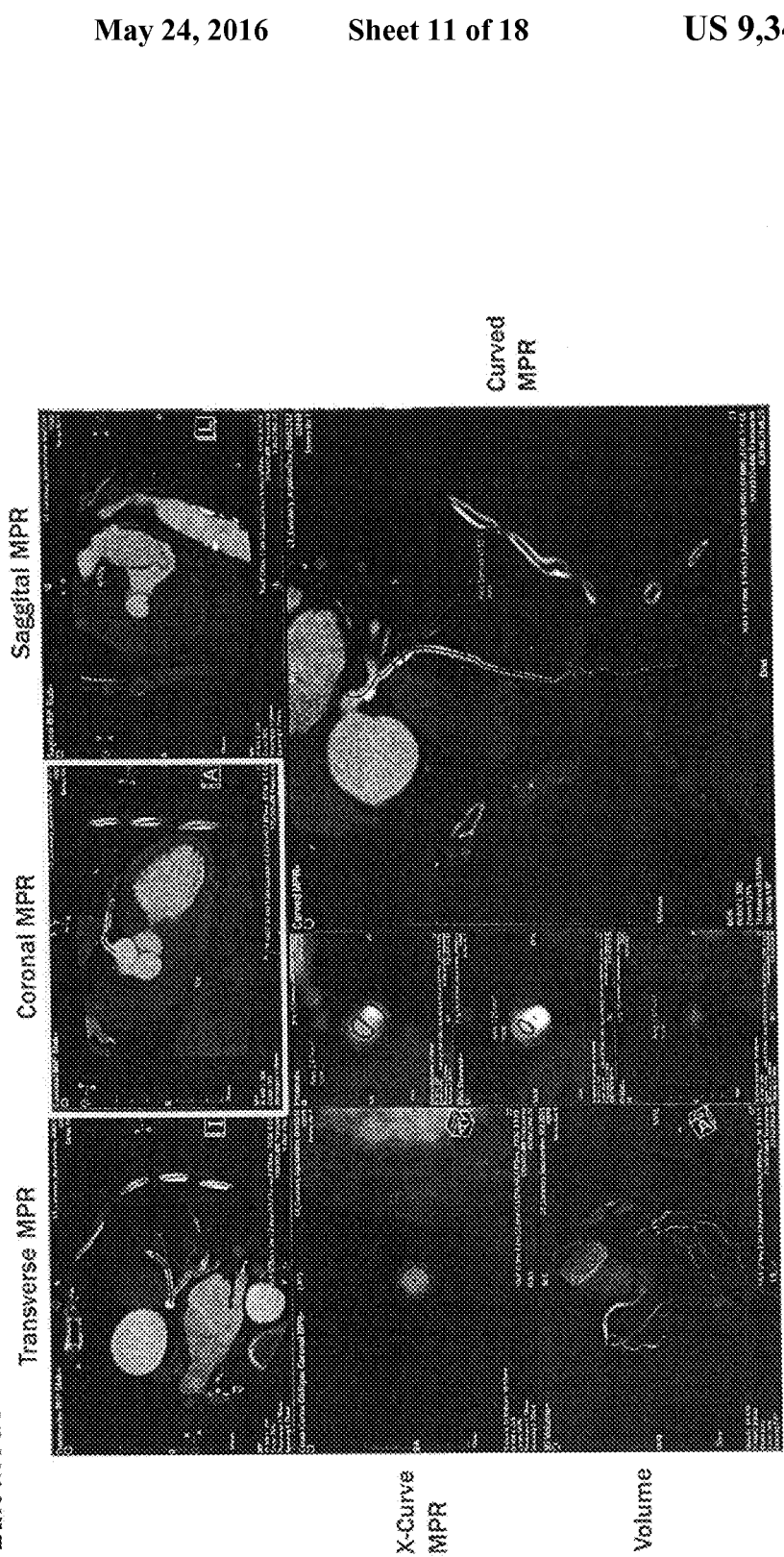

FIG. 9A is a screen shot in the layout of FIG. 4 which illustrates an example layout as presented to the user when browsing to identify if there are any portions of the centerline that need to be corrected. Some errors in the centerline are evident in each of the transverse, coronal and sagittal MPR views. The user selects one of the views for an editing session. In this example it is assumed the user select the coronal MPR view since this is a view which clearly shows the errors to be corrected (apparent as an unrealistic jaggedness in the centerline's path, as would be readily apparent to the informed user), and which shows a major portion of centerline to be edited, including the origin of the coronary vessel. This selection may be done for example, by clicking the cursor on the coronal MPR view while holding down another key that provides a shortcut to a curve editing session.

FIG. 9B is a screen shot of a bespoke simplified layout for the curve editing session in which the selected MPR view occupies the majority of the screen area. In this example, the MPR view is a coronal MPR view at the start of the editing session, although of course this will change with subsequent rotation about the rotation axis parallel to the trend line. Down the left hand side of the layout, a cross-curve MPR view and a curved MPR view are additionally displayed. The trend line is shown displayed in the MPR view, but not in the curved and cross-curve MPR views, although it could be added to one or both of those if desired. As is evident, the trend line only needs to follow the general direction of the portion of centerline to be edited, i.e. the general direction of the underlying lumen in the region where the centerline is to be edited. The nudge tool is also shown in the MPR view of FIG. 9B, indicating that the user has already placed it and is making a correction to the centerline. Three parallel curved arrows also schematically indicate the rotation of the MPR view that the user can make during the editing session, i.e. the rotation around an axis parallel to the trend line and intersecting the more localized portion of the centerline that has been edited by the nudge tool.

FIG. 9C is a view the same as FIG. 9A except incorporating the centerline correction made during the editing session. As can be seen in each of the transverse, coronal and sagittal MPR views, the centerline correction has been accurately performed.

The above description assumes the original centerline was obtained by an automatic centerline finding algorithm. However, it will be appreciated that the method of centerline correction described herein is agnostic to how the centerline has been arrived at, so is equally applicable to centerlines that have been defined by any means, whether automatic or manual.

In the above examples, we refer to the base view as the MPR view, but it could be another view that represents the underlying data in substantially the same form as the underlying data, such as a volume rendered view, i.e. volumetric views such as surface rendering and inverted MIP volume views.

The method as described above will be implemented in software or in a combination of software and optimized or dedicated hardware, such as graphics cards or chip sets suitable for or optimized to volume rendering. The software will be incorporated in a rendering application which may run on a computer workstation or a server which is part of a network operating under a client-server model. The usual context for the workstation or server on which the rendering application is resident will be a hospital network as now described.

Figure 10:
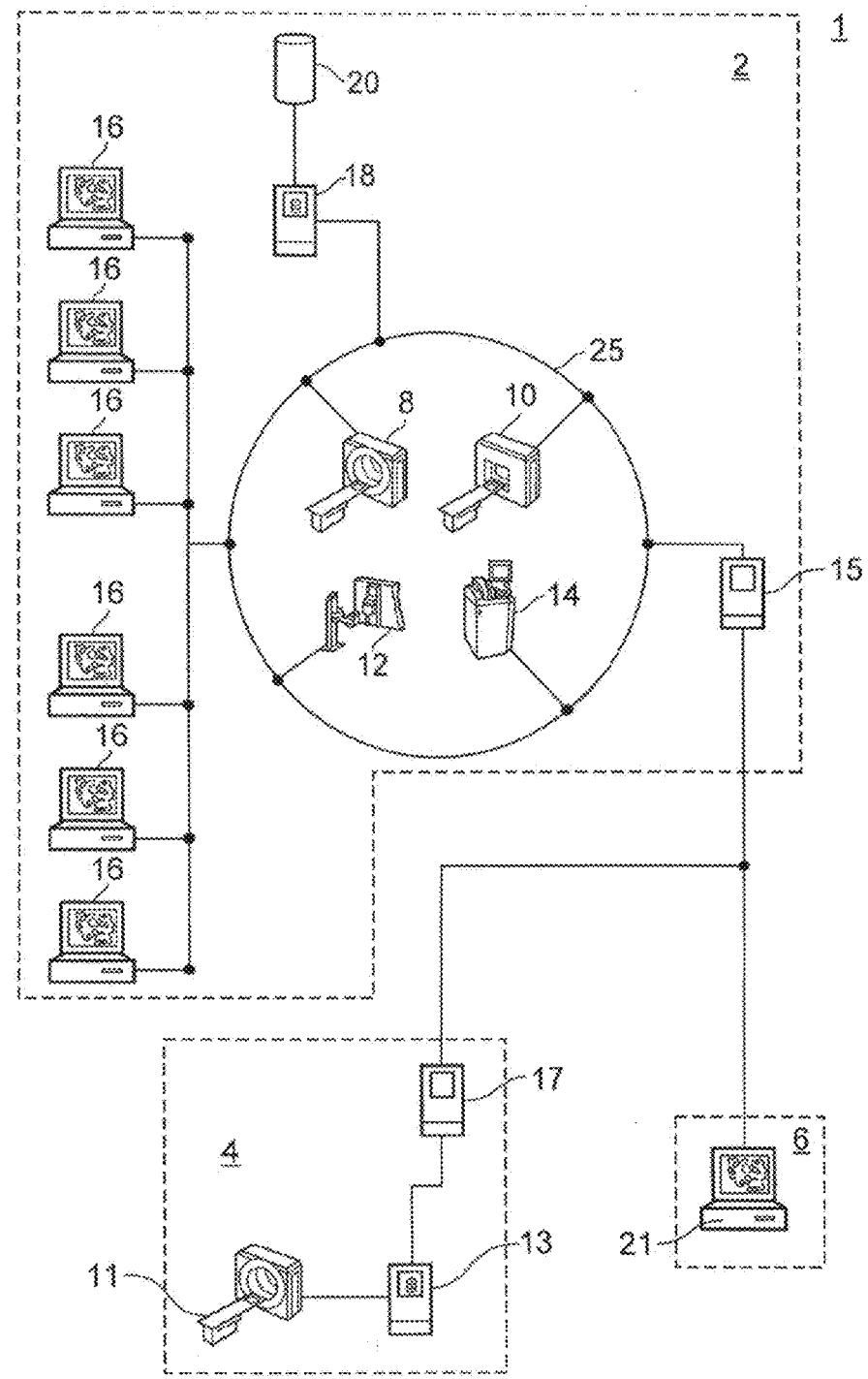
FIG. 10 is a schematic diagram showing an exemplary network of diagnostic devices and associated equipment.

FIG. 10 is a schematic representation of an exemplary network 1 of computer controlled diagnostic devices, stand-alone computer workstations and associated equipment. The network 1 comprises three components. There is a main hospital component 2, a remote diagnostic device component 4 and a remote single user component 6. The main hospital component 2 comprises a plurality of diagnostic devices for acquiring patient images, in this example, a CT scanner 8, a MR imager 10, a digital radiography (DR) device 12 and a computed radiography (CR) device 14, a plurality of computer workstations 16, a common format file server 18, a file archive 20 and an internet gateway 15. All of these features are inter-connected by a local area network (LAN) 25. It will be understood that each computer apparatus has at least one network output connection for communicating over the network.

The remote diagnostic device component 4 comprises a CT scanner 11, a common format file server 13 and an Internet gateway 17. The CT scanner 11 and file server 13 are commonly connected to the internet gateway 17, which in turn is connected via the internet to the internet gateway 15 within the main hospital component 2.

The remote single user component 6 comprises a computer workstation 21 with an internal modem (not shown). The computer workstation 21 is also connected via the Internet to the Internet gateway 15 within the main hospital component 2.

The network 1 is configured to transmit data within a standardized common format. For example, the CT scanner 8 initially generates a source data set, i.e. a 3D image data set, from which an operator may derive an appropriate 2D image. The 2D image is encoded in a standard image data format and transferred over the LAN 25 to the file server 18 for storage on the file archive 20. A user working on one of the computer workstations 16 may subsequently request the image, the file server 18 will retrieve it from the archive 20 and pass it to the user via the LAN 25. Similarly, a user working remotely from the main hospital component 2, either within the remote diagnostic device component 4, or the remote single user component 6, may also access and transmit data stored on the archive 20, or elsewhere on the network 1.

Figure 11:
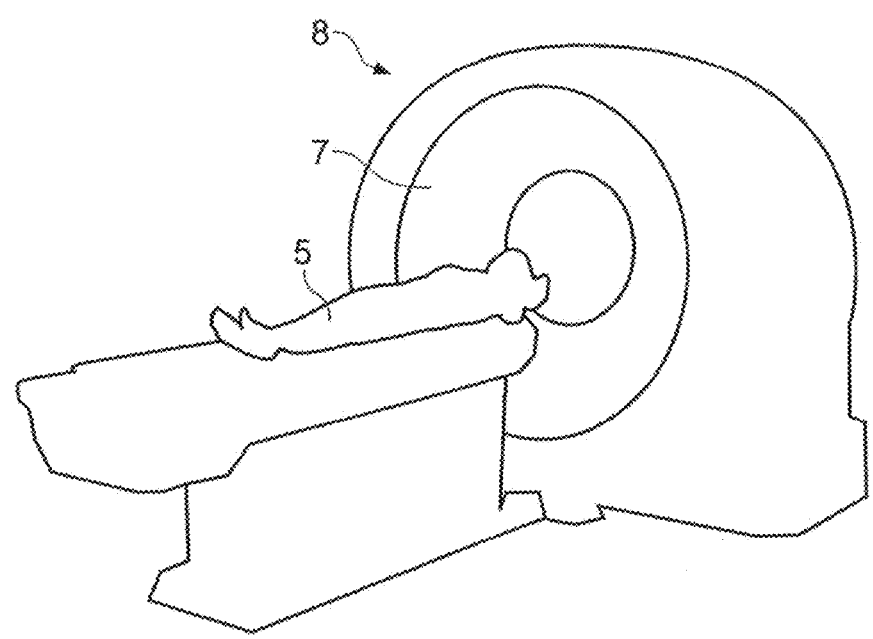
FIG. 11 shows a generic CT scanner for generating volume data.

FIG. 11 is a schematic perspective view of a generic scanner, most especially a computer-assisted tomography (CT) scanner 8 such as represented in FIG. 10, for obtaining cross-sectional images on X-ray attenuation associated with a region of a patient 5 within an opening 7 of the scanner 8.

Different imaging modalities (e.g. CT, MR, PET, ultrasound) may be used to provide different types of medical image data.

With reference to FIG. 10 and FIG. 11, the rendering application embodying the invention may be resident on any of the computer apparatuses shown, namely the workstations 6, 16, the servers 13, 15, 17, 18 or the computers and any associated graphics processing hardware associated with the scanners 8, 10, 11, 12, 14.

Figure 12A:
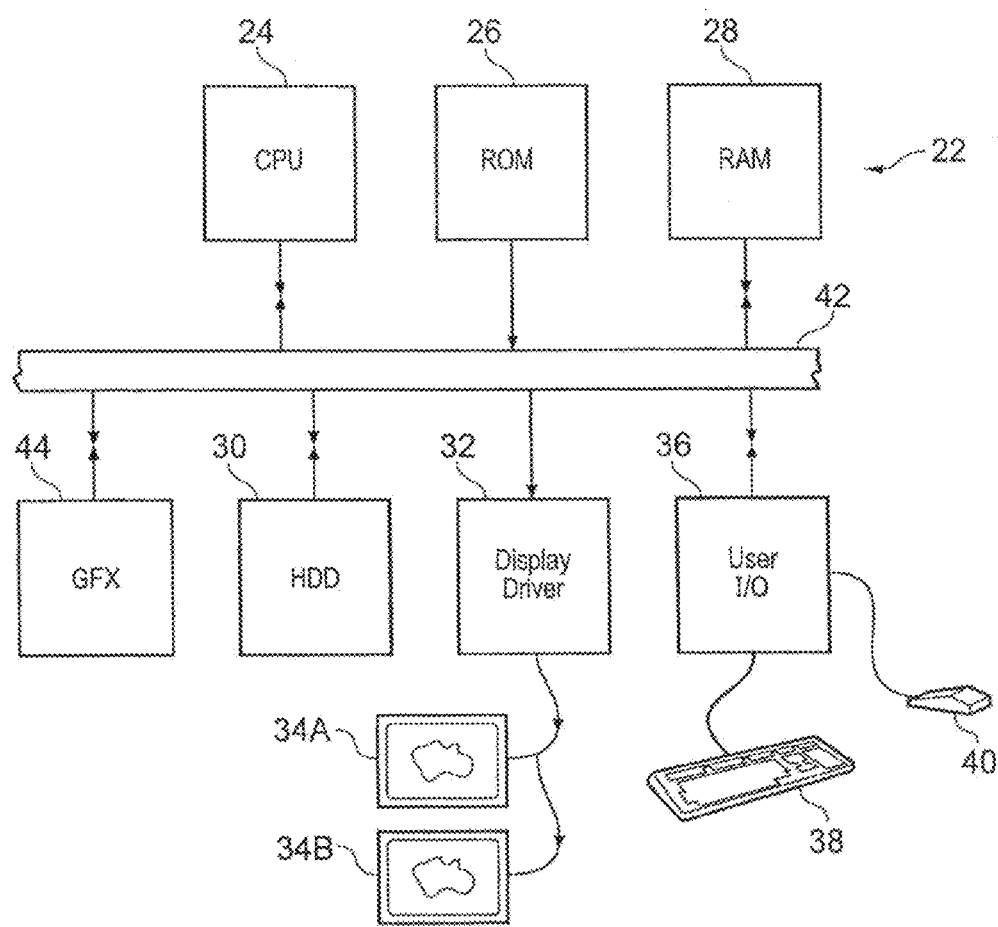
FIG. 12A and FIG. 12B schematically show a computer system for processing image data in accordance with an embodiment of the invention.
Figure 12B:
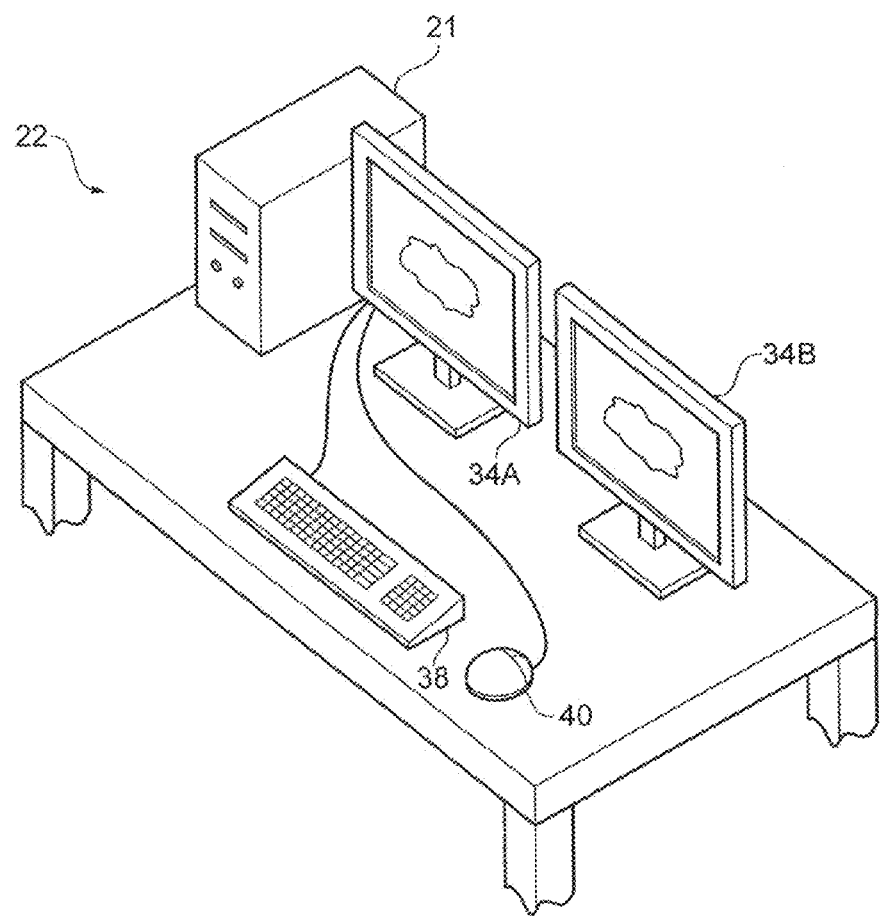

FIGS. 12A and 12B schematically illustrate a general purpose computer system 22 configured to perform processing in accordance with an embodiment of the invention. FIG. 12A primarily represents the functional units comprising the computer system 22 while FIG. 12B is a schematic perspective view showing the computer system 22 arranged for use.

The computer 22 includes a central processing unit (CPU) 24, a read only memory (ROM) 26, a random access memory (RAM) 28, a hard disk drive 30, a display driver 32, and two displays 34, namely a first display 34A and a second display 34B, and a user input/output (IO) circuit 36 coupled to a keyboard 38 and mouse 40. These devices are connected via a common bus 42. The computer 22 also includes a graphics card 44 connected via the common bus 42. The graphics card includes a graphics processing unit (GPU) and random access memory tightly coupled to the GPU (GPU memory).

The CPU 24 may execute program instructions stored within the ROM 26, the RAM 28 or the hard disk drive 30 to carry out processing, display and manipulation of medical image data that may be stored within the RAM 28 or the hard disk drive 30. The RAM 28 and hard disk drive 30 are collectively referred to as the system memory. The CPU 24 may also execute program instructions corresponding to an operating system of the computer system 22. In this respect, the CPU may be considered to comprise various functional units for performing tasks associated with the operation of the computer system 22. The GPU may also execute program instructions to carry out processing image data passed to it from the CPU.

Various functional elements comprising the computer system 22, such as the CPU 24, ROM 26, RAM 28, hard disk 30, display driver 32, user input/output (IO) circuit 36, graphics card 44 and connection bus 42 are contained in an enclosure 21. The two displays 34A, 34B, keyboard 38 and mouse 40 are in this case separate from the enclosure with appropriate wiring connecting them back to the relevant functional elements of the computer system in the enclosure 21. In this respect the computer system 22 of the example embodiment in FIGS. 12A and 12B may be considered as being of a desktop type, although other types of computer system could equally be employed.

Figure 13:
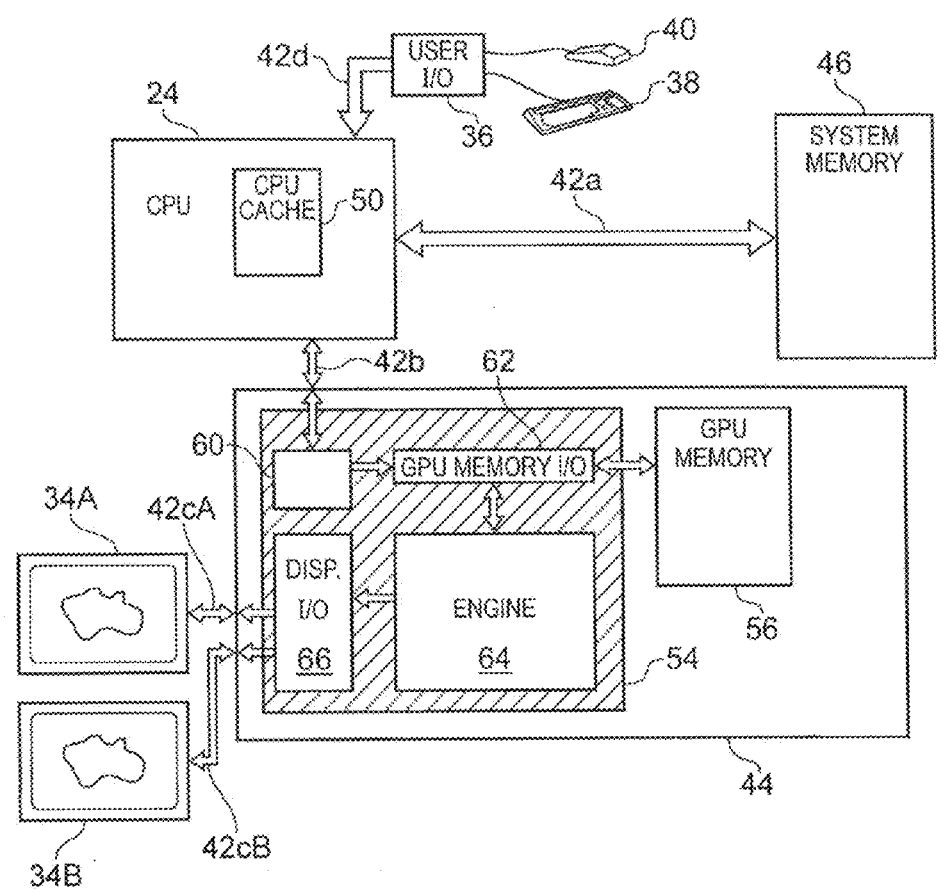
FIG. 13 schematically shows some of the features of the computer system of FIGS. 12A and 12B in more detail.

FIG. 13 schematically shows some of the features of the computer system 2 shown in FIGS. 12A and 12B in more detail. The RAM 28 and hard disk drive 30 are shown collectively as a system memory 46. Medical image data obtained from the scanner 8 shown in FIG. 11 is stored in the system memory as shown schematically in the figure. To assist in showing the different data transfer routes between features of the computer system 22, the common bus 42 shown in FIG. 12A is schematically shown in FIG. 13 as a series of separate bus connections 42a-d. One bus connection 42a connects between the system memory 46 and the CPU 24. Another bus connection 42b connects between the CPU 24 and the graphics card 44. A further pair of bus connections, namely a first bus connection 42cA and a second bus connection 42cB, connects between the graphics card 44 and respective ones of the displays 34A, 34B. Another bus connection 42d connects between the user I/O circuit 36, cursor control unit 27 and the CPU 24. The CPU includes a CPU cache 50. The graphics card 44 includes a GPU 54 and a GPU memory 56. The GPU 54 includes circuitry for providing an accelerated graphics processing interface 60, a GPU cache I/O controller 62, a processing engine 64 and a display I/O controller 66. The processing engine 64 is designed for optimized execution of the types of program instructions typically associated with processing medical image data sets.

A user is able to select desired processing parameters using the keyboard 38 and mouse 40 (or other pointing device, such as a track pad or pen tablet/digitizer) in combination with a graphical user interface (GUI) displayed on the display 34, for example using a movable screen cursor in combination with the mouse, track pad etc. to point and click within respective ones of the first and second displays 34A, 34B.

With reference to FIG. 12A, FIG. 12B and FIG. 13, the rendering application embodying the invention may be stored on HDD 30 and/or ROM 26. When the application is to be run, it can as necessary be loaded into system memory 46 or RAM 28. At run time, faster memory such as cache memory 50, 62 available to the CPU 24 and GPU 54, will also host some of the application. The images output from the rendering application can be displayed on suitable displays, such as first and second displays 34A, 34B. The images output from the rendering application can also be stored in suitable memory. The images output from the rendering application can also be transmitted over the network to be displayed or stored at another location in the network.

Moreover, references to three-dimensional image data sets includes sequences of three dimensional image data sets, such as produced by time-resolved imaging which are sometimes referred to as four-dimensional image data sets. References to three-dimensional image data sets also includes multi-modality data sets, such as combined PET and MR, or combined PET and CT.

Certain embodiments of the invention provide a computer program product, which may be a non-transitory computer program product, bearing machine readable instructions for carrying out the method.

Certain embodiments of the invention provide a computer system loaded with and operable to execute machine readable instructions for carrying out the method.

Certain embodiments of the invention provide an image acquisition device loaded with and operable to execute machine readable instructions for carrying out the method.

Embodiments of the present invention will be described hereinafter and in the context of a computer-implemented system, method and computer program product which may be stored on a non-transitory medium. Although some of the present embodiments are described in terms of a computer program product that causes a computer, for example a personal computer or other form of workstation, to provide the functionality required of some embodiments of the invention, it will be appreciated from the following description that this relates to only one example of some embodiments of the present invention. For example, in some embodiments of the invention, a network of computers, rather than a stand-alone computer, may implement the embodiments of the invention. Alternatively, or in addition, at least some of the functionality of the invention may be implemented by means of special purpose hardware, for example in the form of special purpose integrated circuits (e.g., Application Specific Integrated Circuits (ASICs)).

While certain embodiments have been described, these embodiments have been presented by way of example only, and are not intended to limit the scope of the inventions. Indeed, the novel methods, computers and computer program products and devices described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A computer apparatus comprising: a display and a processor adapted to run a visualization application for visualizing a three-dimensional patient image data set including an anatomical feature of interest, the visualization application being operable to:
   a) display on the display at least one view of the image data set together with a curve which is intended to follow a path relevant for the anatomical feature of interest, but which may include one or more deviations from the path;
   b) initiate an editing session for the curve by selecting a portion of the curve associated with a deviation from the path for correction, the editing session comprising:
      (i) presenting an MPR view including the selected portion of the curve, which has a start point and an end point;
      (ii) defining a trend line which is a straight line passing through the start point and the end point of the selected portion of the curve;
      (iii) amending under user control any desired part of the selected portion of the curve in the MPR view to make corrections to the curve;
      (iv) rotating under user control the MPR view about a rotational axis which is parallel to the trend line in order to permit a user to review the corrections in three dimensions in the image data set;
      (v) iterating under user control the amending and rotating steps as desired to make and review further corrections; and
      (vi) terminating the editing session under user control by accepting or rejecting the corrections; and
   c) display at least one view of the image data set together with the curve incorporating amendments from the editing session.

2. The computer apparatus of claim 1, wherein the visualization application is operable such that as part of initiating an editing session the user selects a particular view from the at least one view of the image data to be presented initially which shows the selected portion of the curve that requires correction.

3. The computer apparatus of claim 1, wherein the anatomical feature of interest is a tubular structure and the anatomical path is a centerline of the tubular structure which the curve is intended to follow.

4. The computer apparatus of claim 1, wherein the rotational axis is offset from the trend line to pass through the vicinity of amended parts of the selected portion of the curve.

5. The computer apparatus of claim 1, wherein the visualization application is operable such that during an editing session the rotational axis is free to move to remain in intersection with, or close to intersection with, amended parts of the selected portion of the curve.

6. The computer apparatus of claim 1, wherein the visualization application is operable such that the trend line is automatically computed from points on the curve at either end of the selected portion of the curve.

7. The computer apparatus of claim 1, wherein the visualization application is operable such that during the editing session the MPR view is presented on the display along with a curved MPR view and/or a cross-curve MPR view updated to follow said rotation.

8. The computer apparatus of claim 1, wherein the visualization application is further operable to store in memory associated with the computer apparatus the three-dimensional patient image data set with an indication of the curve in its edited form, or to output the three-dimensional patient image data set with an indication of the curve in its edited form for external storage.

9. The computer apparatus of claim 1, wherein the visualization application is operable such that the amending is carried out with a graphical user interface control using a circle of adjustable diameter as a geometric construct, the circle being translatable in the plane of the MPR view to come into contact with the curve, whereupon the curve is amended to conform to the contacting edge portion of the circle.

10. A non-transitory computer program product storing the visualization application of claim 1.

11. An image acquisition device loaded with and operable to execute the visualization application of claim 1.

12. A computer-automated method of running a visualization application on a computer apparatus to visualize a three-dimensional patient image data set including an anatomical feature of interest, the method comprising:
   a) displaying at least one view of the image data set together with a curve which is intended to follow a path relevant for the anatomical feature of interest, but which may include one or more deviations from the path;
   b) initiating an editing session by selecting a portion of the curve associated with a deviation from the path for correction, the editing session comprising:
      (i) presenting an MPR view including the selected portion of the curve, which has a start point and an end point;
      (ii) defining a trend line which is a straight line passing through the start point and the end point of the selected portion of the curve;
      (iii) amending under user control any desired part of the selected portion of the curve in the MPR view to make corrections to the curve;
      (iv) rotating under user control the MPR view about a rotational axis which is parallel to and apart from the trend line in order to permit a user to review the corrections in three dimensions;
      (v) iterating under user control the amending and rotating steps as desired to make and review further corrections; and
      (vi) terminating the editing session under user control by accepting or rejecting the corrections; and then
   c) displaying at least one view of the image data set together with the curve incorporating amendments from the editing session.

13. The method of claim 12, wherein, as part of initiating an editing session, the user selects a particular view from the at least one view of the image data to be presented initially which shows the selected portion of the curve that requires correction.

14. The method of claim 12, wherein the anatomical feature of interest is a tubular structure and the anatomical path is a centerline of the tubular structure which the curve is intended to follow.

15. The method of claim 12, wherein the rotational axis is offset from the trend line to pass through the vicinity of amended parts of the selected portion of the curve.

16. The method of claim 12, wherein during an editing session the rotational axis is free to move to remain in intersection with, or close to intersection with, amended parts of the selected portion of the curve.

17. The method of claim 12, wherein the trend line is automatically computed from points on the curve at either end of the selected portion of the curve.

18. The method of claim 12, wherein during the editing session the MPR view is presented on the display along with a curved MPR view and/or a cross-curve MPR view updated to follow said rotation.

19. The method of claim 12, further comprising: storing the three-dimensional patient image data set with an indication of the curve in its edited form.

20. The method of claim 12, wherein said amending is carried out with a graphical user interface control using a circle of adjustable diameter as a geometric construct, the circle being translatable in the plane of the MPR view to come into contact with the curve, whereupon the curve is amended to conform to the contacting edge portion of the circle.

21. A computer apparatus comprising: a display and a processor adapted to run a visualization application for visualizing a three-dimensional patient image data set including an anatomical feature of interest, the visualization application being operable to:
    a) display on the display at least one view of the image data set together with a curve which is intended to follow a path relevant for the anatomical feature of interest, but which may include one or more deviations from the path;
    b) initiate an editing session for the curve by selecting a portion of the curve associated with a deviation from the path for correction, the editing session comprising:
        (i) presenting an MPR view including the selected portion of the curve;
        (ii) defining a trend line which approximately follows the anatomical path in the vicinity of the selected portion of the curve;
        (iii) amending under user control any desired part of the selected portion of the curve in the MPR view to make corrections to the curve;
        (iv) rotating under user control the MPR view about a rotational axis which is parallel to and apart from the trend line in order to permit a user to review the corrections in three dimensions in the image data set;
        (v) iterating under user control the amending and rotating steps as desired to make and review further corrections; and
        (vi) terminating the editing session under user control by accepting or rejecting the corrections; and
    c) display at least one view of the image data set together with the curve incorporating amendments from the editing session.

* * * * *